United States Patent [19]

Isaacson et al.

[11] Patent Number: 4,895,150
[45] Date of Patent: Jan. 23, 1990

[54] IMPLANTED POWER SOURCE

[75] Inventors: Milton S. Isaacson; Anthony P. Lioi, both of Dayton; Gregory A. Thompson, Huber Heights; Donald D. Kinsworthy, Dayton, all of Ohio

[73] Assignee: Nu-Tech Industries, Inc., Dayton, Ohio

[21] Appl. No.: 172,654

[22] Filed: Mar. 24, 1988

[51] Int. Cl.[4] .............................................. A61N 1/36
[52] U.S. Cl. .............................................. 128/419 R
[58] Field of Search ............ 128/419 P, 419 B, 419 R; 600/16, 29–31; 604/175

[56] References Cited

U.S. PATENT DOCUMENTS

| | | | |
|---|---|---|---|
| 4,010,760 | 3/1977 | Kraska et al. | 128/419 PS |
| 4,230,096 | 10/1980 | Zeff et al. | 128/898 |
| 4,333,469 | 6/1982 | Jeffcoat et al. | 128/784 |
| 4,471,783 | 9/1984 | Buffet | 128/419 PS |
| 4,581,020 | 4/1986 | Mittleman | 604/175 |
| 4,673,394 | 6/1987 | Fenten et al. | 604/175 |
| 4,701,180 | 10/1987 | Kelly et al. | 604/175 X |
| 4,772,264 | 9/1988 | Von Hoff et al. | 604/175 |
| 4,778,452 | 10/1988 | Moden et al. | 604/175 X |

OTHER PUBLICATIONS

Watson et al., "Subcutaneous Culture Chamber –...", The Lancet, Jan. 15, 1983, pp. 99–100 (604/175).
Abstract "Biological Effects of Implanted Nuclear Energy Sources for Artificial Heart Devices", National Heart, Lung and Blood Institute, (DTBCM), Dec. 1978, pp. 21 & 22.
Abstract "Implanted Energy Conversion System", National Heart, Lung and Blood Institute (DTBCM), Dec. 1978, pp. 23 & 24.
Abstract "Development of Percutaneous Energy Transmission Systems", National Heart, Lung and Blood Institute (DTBCM), Dec. 1978, pp. 45 and 46.
Portion of an Abstract, National Heart, Lung and Blood Institute (DTBCM), Dec. 1973, p. 112, with diagram entitled "System 8 Clinical Implant Concept".
Abstracts "Thermal Ventricular Assists System" & Development of a Thermal Ventricular Assist System (TVAS), National Heart, Lung and Blood Institute (DTBCM), Dec. 1985, pp. 77 & 78.
Article "An Electric Motor Driven Total Artificial Heart", by G. Rosenberg et al., Institute of Electrical & Electronics Engineers, 1982.
Article "A Cam-Type Electric Motor–Driven Left Ventricular Assist Device", by G. Rosenberg et al., Journal of Biomechanical Engineering, Aug. 1982.
Article "A Roller Screw Drive for Implantable Blood Pumps", by G. Rosenberg et al., Transactions of the American Society of Artificial Internal Organs, vol. 28, 1982, pp. 123–126.
Article "The Development of an Electrohydraulic Implantable Artificial Heart", by W. H. Burns et al., The American Society of Artificial Internal Organs, 1965, pp. 265–270.

*Primary Examiner*—Max Hindenburg
*Assistant Examiner*—J. Lacyk
*Attorney, Agent, or Firm*—Wood, Herron & Evans

[57] ABSTRACT

A housing for enclosing a power source for operating an implanted artificial organ is provided. The housing has an annular rim defining an aperture and is mounted in the human body such that replacement of the power source through the aperture is effected from outside the body without resort to surgical means. The housing is secured in the body by attachment to internal tissue, preferably bone.

9 Claims, 1 Drawing Sheet

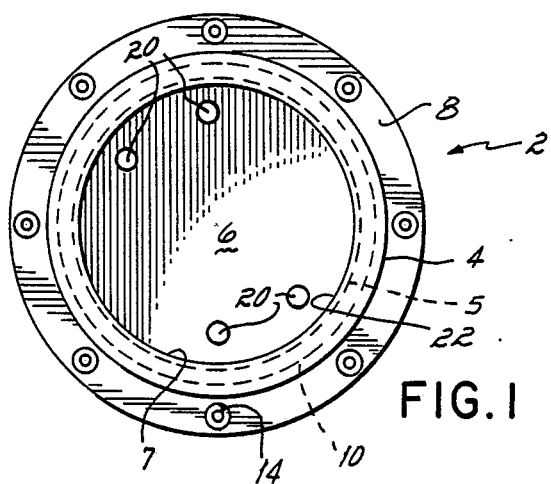
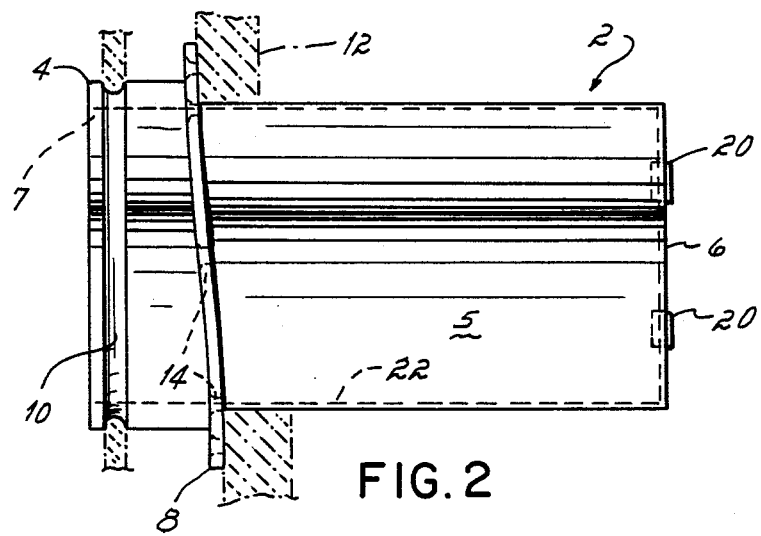
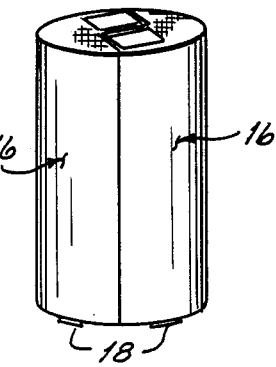
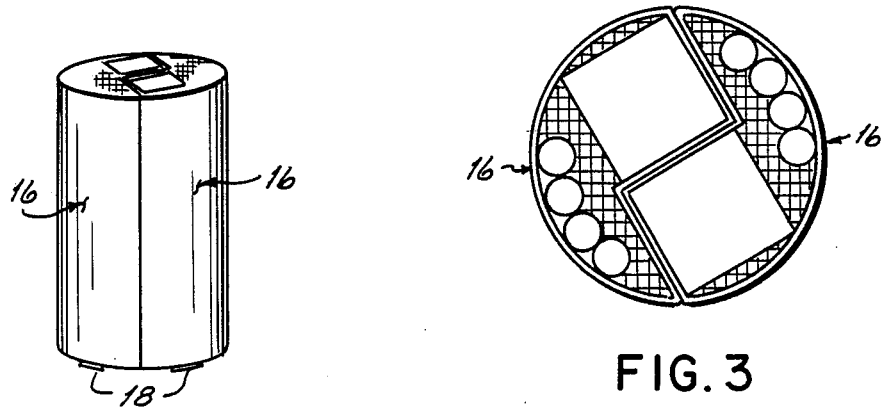

IMPLANTED POWER SOURCE

FIELD OF THE INVENTION

This invention relates to power source housings and the power sources contained therein which are mounted in the human body in such manner as to permit replacement of the power source by non-surgical means.

BACKGROUND OF THE INVENTION

The use of devices implanted in the body to supplement or even supplant the operation of the body's own natural organs has expanded dramatically in recent times. An essential component of the implanted devices has been, and continues to be, the power source supplying energy to the device.

Early efforts in the area of artificially supplementing or supplanting body functions were directed toward regulating the rhythmic beating of an otherwise healthy heart. Stimulating units which operated at specified beat rates, known as pacemakers, were surgically implanted into the body and attached to the heart. On a signal from the pacemaker, the heart would contract and thereby pump blood through the circulatory system. Power for the pacemaker was supplied by a battery having long operating duration, the battery being implanted under the skin. Replacement of this battery required further surgery.

The pacemaker could substantially restore a normal life-style to a patient having a fundamentally sound, yet irregularly beating heart. However, for those having a damaged, defective or diseased heart, until recently the options were limited to either a regimen of bed rest and medication or heart transplant.

A significant recent advance in heart care has been the development of an artificial heart. The artificial heart functions as a total replacement for the natural organ, and recently was shown to provide many additional months of life to a man who otherwise would not have lived. However, the total artificial heart presently requires so much peripheral support equipment as to make the recipient a virtual prisoner to that equipment.

Where the heart is still able to function but yet is inadequate to handle the demands of normal activities, mechanical devices are now available to assist the function of the natural organ. These devices, known as ventricular assist systems, improved the ability of the natural heart to pump oxygenated blood to the rest of the body. The assist systems augment the natural heart by assuming the pumping function of the left ventricle, thereby forcing oxygenated blood from the ventricle through the body's circulatory system.

Systems have been developed having a peripheral power source which fits inside a carrying case having a shoulder strap, permitting the user of the assist system a larger degree of mobility. The power source is rechargeable and easily replaceable, as a practical concession to the requirement that the source be both portable and yet capable of supplying the relatively large power consumption requirements of the implanted device. The implanted assist device is connected to the peripheral equipment by means of a cable bundle running from the implanted system through the skin to the outside. The use of the portable power supply restores the wearer to a nearly normal level of mobility. However, the portable power supply requires that the wearer constantly carry it with him. Further, the cable bundle running through the skin must be handled with extreme care to minimize the possibility of infection or of damage to the skin and underlying tissues in proximity to the bundle. Also the cable bundle is relatively bulky, imposes an unnatural appearance on the body, and requires that caution be exercised when clothes are worn over the bundle.

BRIEF DESCRIPTION OF THE INVENTION

It is an object of the invention to provide a power supply to a replacement heart that gives the patient a life of substantially normal activity, free from the burden of a detached conductor connected power supply.

It is a further object of the invention to provide a mounting for a power supply for implanted artificial organs wherein the supply housing is located predominantly inside the body with a portion accessible from the outside.

It is yet a further object that the housing be able to be securely fastened to the body tissue.

These and other objects and advantages are attained by providing a power supply unit consisting of a cup shaped housing and a power supply contained therein. In the preferred embodiment, the housing contains two independently removable power supplies to permit replacement of one power supply without interrupting the flow of energy to the implanted artificial organ. The housing preferably is rigid and has an annular flange which permits securing to bone tissue. In the preferred embodiment, the rigid cup shaped housing having an annular flange is fitted through an incision in the skin and into a hole drilled in the hip bone. Preferably, the flange is shaped in such manner as to conform to the contours of the mating surface of the hip bone. In this position the rigid housing is able to provide additional support to the hip bone while causing minimal interference with the adjacent natural organs. The flange is secured to the bone by bolts or adhesive.

The housing is secured in such a way that the rim of the cup extends through the incision in the skin. The preferred independently removable power supplies are then fitted into the cup. Fuel cell power supplies provide maximum duration operation of the implanted artificial organ, but batteries are also usable. Electrical connection from the implanted artificial organ is made to contacts on the housing which mate with electrodes on the inserted power supplies.

A power supply and housing of this type permits the use of artificial, electrically-driven implant devices with virtually no outward indication that such devices are actually in place. The absence of a cable bundle external to the body permits the person to wear clothing without the need to compensate for the telltale bulge. Also, the possibility of damage to the skin and underlying tissues at the point where the cable would come through would be decreased, due to the fact that there is no cable that could be snagged. Thus, there is a significant reduction in the risk of applying large stresses to the device/tissue interface that could damage the tissue attachment The power supply is designed to be easily replaced, thus rendering the replacement operation less burdensome and permitting use of more compact, albeit shorter-lifetime power supplies.

BRIEF DESCRIPTION OF THE DRAWINGS

FIG. 1 is a top plan view of the power source housing.

FIG. 2 is a side elevational view of the power source housing depicting the relationship of the housing to body tissue after insertion of the housing.

FIG. 3 is a top plan view of two paired power sources.

FIG. 4 is a perspective view of the paired power sources.

DETAILED DESCRIPTION OF THE INVENTION

Referring to FIGS. 1 and 2, the power supply of the present invention has a housing 2 which is impervious to the flow of internal body fluids. The housing is preferably cup shaped and has an annular end rim 4, cylindrical walls 5 and a bottom wall 6. The rim 4 creates an aperture 7. A securing flange 8 and a channel 10 is formed in the cylindrical wall between the flange 8 and rim 4.

The bottom wall 6 of the housing 2 in the preferred embodiment is inserted through an incision in the skin and fitted through a hole of sufficient circumference drilled through the hip bone 12. The drilled hole is large enough to accept the bottom wall 6, but further insertion is prohibited at the point where the securing flange 8 contacts the hip bone tissue It is preferred that the securing flange 8 be molded or formed in a shape which conforms to the contours of the contacting hip bone tissue. The flange is bolted or screwed to the hip bone through securing holes 14. Eight securing holes 14 are shown in FIG. 1, permitting fastening at eight points. However, circumstances may dictate that fewer or greater securing points are necessary to adequately affix the housing 2 to bone tissue. Alternatively, the flange 8 may be secured to bone tissue by means of adhesive or cement applied to the interface.

Subsequent to the securement of the housing 2 to bone tissue, the skin tissue is directed into the channel 10 between securing flange 8 and end rim 4. End rim 4 will thus extend outside the body, or lie in the plane of the body's skin and will permit easy access to aperture 7. Excess skin tissue is trimmed away to improve the appearance of the body at the site of the inserted housing 2. In order to prohibit a sinus tract from forming at the boundary of the skin and housing 2, the surface of the housing 2 which contacts body tissue in the preferred embodiment is modified to promote sealing to the adjacent body tissue. The modified surface has a large number of pores which are able to accept body tissue. In time, the body tissue grows into the multicellular array of pores and locks the housing into position connected to adjacent tissue. Though sealing is most important where the dermal and epidermal skin layers contact the housing 2, it is preferred that the housing 2 seal or adhere to body tissue over its entire contacting surface.

Where the housing 2 is fitted into a hole drilled through the hip bone, the housing 2 must be sufficiently rigid to compensate for the loss in structural integrity occasioned by the removal of bone tissue. To this end the housing 2 is constructed from materials such as, but not limited to, polycarbonate resin (Lexane ®) or titanium, which have sufficient structural strength and are unaffected by contact with body tissues. The housing 2 constructed from rigid materials may also be inserted into other areas of the body where space permits, such as the rib cage region.

Alternatively, the housing 2 may be constructed from a flexible material to form a sac which may be inserted into the body. The sac-like housing would be capable of conforming to available spaces underneath the skin without the need for drilling through bone tissue.

The power source 16 is preferably a fuel cell, but a battery or other power source may be used. Where the housing is produced from flexible material, the power source would have a shape which would achieve optimum conformance with body contour. The power source 16 fits into housing 2 by guides and has electrodes 18 shown in FIG. 4 which mate with electrical contacts 20 sealed onto the bottom wall 6 of the housing 2 to permit transfer of current from the power source 16 to the implanted artificial organ (not shown). In the preferred embodiment, the housing 2 contains two power sources 16 connected in parallel, supplying energy to the artificial organ. The use of two power sources permits removal o one source while still supplying energy to the implanted artificial organ such that the organ's operation is not interrupted. FIG. 3 shows the individual power sources 16 having a "Z"-shaped configuration, though this particular shape is not required. Replacement of the power source 16 can be effected simply and quickly because the mating surface 22 on the housing 2 is external to the body. The power sources 16 when in position form a watertight seal between each other and the housing 2 to permit the wearer to bathe or engage in watersports without fear of damaging the power source. The power sources 16 are fixed into the housing 2 by securing means (not shown) which will require a positive manual act on the part of the wearer to effect removal. The securing means prevent accidental loss of contact between the electrodes 18 and the electrical contacts 20, thereby assuring uninterrupted operation of the artificial organ.

The housing 2 must have dimensions sufficient to accept a power source 16 having sufficient energy to power the intended implanted device for a reasonable period of time, typically 24 hours at minimum, but preferably for a time in excess of 24 hours to provide a safety factor for the wearer. The size of the power source will vary depending on the energy demands of the implanted device. Where the artificial organ is a left ventricular assist device, two power sources 16 providing approximately 32 hours of organ operation would have a dimension of approximately 3 inches in circumference by approximately 5.87 inches long. The mated power source combination provides approximately 15 watts power at 12 volts.

The housing 2 typically is implanted in the same operation with the power-consuming implanted artificial organ, and electrical connection between the housing and the organ is effected. The power sources 16 are inserted into the housing 2 and energy is supplied to the artificial organ. Preferably once each day, the power sources 16 are changed. First, one power source is removed and replaced. Then, the second power source is removed and replaced. This procedure ensures that an uninterrupted supply of energy is provided to the implanted artificial organ.

This specification has described the present invention and its operating parameters. Variations may be achieved without departing from the spirit and scope hereof as defined by the claims.

We claim:

1. The method of mounting a power supply in a human body comprising the steps of:
   forming a hole in the skin;

inserting a cup shaped housing having an annular rim surrounding an aperture such that said rim extends outside the skin;
securing said housing to body tissue comprising bone matter at least in part; and
removably inserting a power supply into said aperture.

2. The method of mounting a power supply in a human body comprising the steps of:
forming a hole in a hip bone;
inserting a cup shaped housing having a flange through said hole;
fixing said flange to said hip bone, so that said cup is accessible from outside the body; and,
removably inserting a power supply in said cup shaped housing.

3. The method of claim 2 wherein said flange conforms to the contours of said hip bone.

4. The method of claim 2 further wherein said cup shaped housing is rigid.

5. A power supply unit for an artificial internal organ comprising:
a cup shaped housing impervious to the flow of internal body fluids having a flange for attachment to body tissue comprising bone material at least in part, said housing having an annular rim extending outwardly from said flange for attachment to the outside of the skin said housing having an interior surface and an exterior surface, said cup shaped housing being adapted to be mounted on a living body with the exterior surface extending into said body and said interior surface accessible from outside said body;
conductors passing through said housing and being exposed at said interior surface; and
a source of electrical power removably disposed in said housing and electrically connected to said conductors.

6. The power supply unit of claim 5 wherein said cup shaped housing is rigid.

7. The power supply unit of claim 5 further comprising two said sources of electrical power removably disposed in said housing and connected in parallel to permit a continuous supply of power to said artificial internal organ during replacement of said sources.

8. The power supply unit of claim 5 further comprising said cup shaped housing having an annular channel on said exterior surface disposed adjacent to the rim of said housing.

9. The power supply unit of claim 5 wherein said flange conforms to the contours of the hip bone of a human body.

* * * * *